United States Patent [19]

Bernardin

[11] Patent Number: 5,789,180
[45] Date of Patent: Aug. 4, 1998

[54] DETECTION OF WHEAT THAT HAS EXPERIENCED ELEVATED TEMPERATURES DURING THE GRAIN FILLING PERIOD

[75] Inventor: John E. Bernardin, El Sobrante, Calif.

[73] Assignee: The United States of America as represented by the Secretary of Agriculture, Washington, D.C.

[21] Appl. No.: 543,233

[22] Filed: Oct. 13, 1995

Related U.S. Application Data

[63] Continuation of Ser. No. 192,873, Feb. 7, 1994, abandoned.

[51] Int. Cl.$^6$ .......................... G01N 33/53; G01N 33/68
[52] U.S. Cl. .......................... 435/7.8; 435/7.1; 435/7.27; 435/7.92; 435/7.94; 435/7.95; 436/518; 436/536; 436/548; 436/86; 436/87
[58] Field of Search .................. 435/7.1, 7.2, 7.8, 435/7.92, 7.93, 7.94, 7.95, 970, 287.2, 287.9, 975, 288.3, 805; 436/518, 536, 548, 86, 87; 422/55, 56, 57, 61

[56] References Cited

U.S. PATENT DOCUMENTS

| | | | |
|---|---|---|---|
| 4,891,313 | 1/1990 | Berger et al. | 436/518 |
| 5,120,643 | 6/1992 | Ching et al. | 435/7.94 |

OTHER PUBLICATIONS

Goding, 1983, *Monoclonal Antibodies: Principles and Practices* Academic Press, London, pp. 40–43.
Chen, et al., 1990, J Cell Biol 110:1873–1883.
Affinity BioReagents, Product Data: *Catalog Number MA3–006.*
Inwood et al., 1990. Affect of heat stress on the pattern of protein synthesis in wheat endosperm. Plant Physiol 93 (1 Suppl.):88. Abstract #513.
Dewey et al., 1991. Antibodies in plant science. Acta Botanica Neerlandica 40: 1–27.
Hellstrom et al. 1985. In *Monoclonal Antibodies for Cancer Detection and Therapy* (Baldwin et al, eds). Academic Press, London p. 20.
S. Lindquist, "The Heat–Shock Response," *Annual Review of Biochemistry* 55:1151–1191 (1986).
R. A. Vierling, and H. T. Nguyen, "Heat–Shock Protein Synthesis and Accumulation in Diploid Wheat," *Crop Science* 30:1337–1342 (1990).
M. Zivy, "Genetic Variability for Heat Shock Proteins in Common Wheat," *Theoretical and Applied Genetics* 74:209–213 (1987).
W. J. Welch, and J. P. Suhan, "Cellular and Biochemical Events in Mammalian Cells during after Recovery from Physiological Stress," *Journal of Cell Biology* 103:2035–2053 (1986).

(List continued on next page.)

*Primary Examiner*—Paula K. Hutzell
*Assistant Examiner*—James L. Grun
*Attorney, Agent, or Firm*—M. Howard Silverstein; John D. Fado; Margaret A. Connor

[57] ABSTRACT

Methods for detecting heat-stressed wheat, that is, wheat that has experienced elevated temperatures during the grain filling period, and methods to assess end-use properties of wheat grain are disclosed. In the method to detect heat-stressed wheat, wheat heat stress peptide in a sample of wheat grain or flour is measured. Wheat grain or flour that has a level of wheat heat stress peptide two or more times greater that the constitutive level is determined to have experienced elevated temperatures during the grain filling period. In the method to assess an end-use property of wheat, wheat heat stress peptide in a sample of wheat grain or flour is measured, and the level is compared to a calibration curve that correlates the level of wheat heat stress peptide and the end-use property.

8 Claims, 6 Drawing Sheets

OTHER PUBLICATIONS

R. P. Beckmann, L. A. Mizzen, and W. J. Welch, "Interaction of Hsp 70 with Newly Synthesized Proteins: Implications for Protein Folding and Assembly," *Science* 248:850–854 (1990).

J. A. Miernyk, N. B. Duck, R. G. Shatters, Jr., and W. R. Folk, "The 70–Kilodalton Heat Shock Cognate Can Act as a Molecular Chaperone during the Membrane Translocation of a Plant Secretory Protein Precursor," *The Plant Cell* 4:821–829 (1992).

E. B. Fontes, B. B. Shank, R. L. Wrobel, S. P. Moose, G. R. OBrian, E. T. Wurtzel, and R. S. Boston, "Characterization of an Immunoglobulin Binding Protein Homolog in the Maize floury–2 Endosperm Mutant," *The Plant Cell* 3:483–496 (1991).

X. Li, Y. Wu, D–Z. Zhang, J. W. Gillilikin, R. S. Boston, V. R. Fraceschi, and T. W. Okita, "Rice Prolamine Protein Body Biogenesis: A BiP–Mediated Process," *Science* 262:1054–1055 (1993).

C. K. Kassenbrock, P. D. Garcia, P. Walter, and R. B. Kelly, "Heavy–chain Binding Protein Recognizes Aberrant Polypeptides Translocated in vitro," *Nature* 333:90–93 (1988).

H–L. Chaing, S. R. Terlecky, C. P. Plant, and J. F. Dice, "A Role for a 70–Kilodaton Heat Shock Protein in Lysosomal Degradation of Intracellular Proteins," *Science* 246:382–385 (1989).

C. S. Blumenthal, F. Bekes, I. L. Batey, C. W. Wrigley, H. J. Moss, D. J. Mares, and E. W. Barlow, "Interpretation of Grain Quality Results from Wheat Variety Trials with Reference to High Temperature Stress," *Australian Journal of Agricultural Research* 42:325–334 (1991).

C. S. Blumenthal, E. W. Barlow, and C. W. Wrigley, "Growth Environment and Wheat Quality: the Effect of Heat Stress on Dough Properties and Gluten Proteins," *Journal of Cereal Science* 18:3–21 (1993).

C. S. Blumenthal, I. L. Batey, C. W. Wrigley, and E. W. Barlow, "Involvement of a Novel Peptide in the Heat Shock Response of Australian Wheats," *Australian Journal of Plant Physiology* 17:441–449 (1990).

S. Giorini and G. Galili, "Characterization of HSP–70 Cognate Proteins from Wheat," *Theoretical and Applied Genetics* 82:615–620 (1991).

W. J. Welch and J. R. Feramisco, "Rapid Purification of Mammalian 70,000–Dalton Stress Proteins: Affinity of the Proteins for Nucleotides," *Molecular and Cellular Biology* 5:1229–1237 (1985).

C. S. Blumenthal, I. L. Batey, F. Bekes, C. W. Wrigley, and E. W. Barlow, "Gliadin Genes Contain Heat–shock Elements: Possible Relevance to Heat–induced Changes in Grain Quality," *Journal of Cereal Science* 11:185–187 (1990).

C. Blumenthal, F. Bekes, C. W. Wrigley, and E. W. Barlow, "The Acquisition and Maintenance of Thermotolerance in Australian Wheats," *Australian Journal of Plant Physiology* 17:37–47 (1990).

R. S. Boston, E. P. Fontes, B. B. Shank, and R. L. Wrobel, "Increased Expression of the Maize Immunoglobulin Binding Protein Homolog b–70 in Three Regulatory Mutants," *The Plant Cell* 3:497–505 (1991).

P. du Jardin, C. Lejour, and J–M. Jacquemin, "Heat Shock RNAs in Leaf and Root Explants of Wheat," *Plant Physiology and Biochemistry* 28:183–189 (1990).

K. W. Helm and R. H. Abernethy, "Heat Shock Proteins and Their mRNAs in Dry and Early Embibing Embryos of Wheat," *Plant Physiology* 93:1626–1633 (1990).

K. L. Hendershot, J. Weng, and H. T. Nguyen, "Induction Temperature of Heat–Shock Protein Synthesis in Wheat," *Crop Science* 32:256–261 (1992).

C. J. Howarth, "Molecular Responses of Plants to an Increased Incidence of Heat Shock," *Plant, Cell and Environment* 14:831–841 (1991).

A. Marocco, A. Santucci, S. Cerioli, M. Motto, N. Di Fonzo R. Thompson, and F. Salamini, "Three High–Lysine Mutations Control the Level of ATP–Binding HSP70–like Proteins in the Maize Endosperm," *The Plant Cell* 3:507–515 (1991).

E. F. McElwain, and S. Spiker, "Molecular and Physiological Analysis of a Heat–Shock Response in Wheat," *Plant Physiology* 99:1455–1460 (1992).

A. Necchi, N. E. Pogna, and S. Mapelli, "Early and Late Heat Shock Proteins in Wheats and Other Cereal Species," *Plant Physiology* 84:1378–1384 (1987).

D. R. Porter, H. T. Nguyen, and J. J. Burke, "Chromosomal Location of Genes Controlling Heat Shock Proteins in Hexaploid Wheat," *Theoretical and Applied Genetics* 78:873–878 (1989).

R. A. Vierling and H. T. Nguyen, "Heat–Shock Protein Gene Expression in Diploid Wheat Genotypes Differing in Thermal Tolerance," *Crop Science* 32:370–377 (1992).

W. C. Wang and H. T. Nguyen, "Thermal Stress Evaluation of Suspension Cell Cultures in Winter Wheat," *Plant Cell Reports* 8:108–111 (1989).

M. C. Wilkinson, P. A. Wheatley, C. J. Smith, and D. L. Laidman, "Higher Plant Heat–Shock Protein 70: Purification and Immunochemical Analysis," *Phytochemistry* 29:3073–3080 (1990).

ARAPAHOE

| UNHEATED | HEATED |
|---|---|
| 1   .5   .25   .125   .0625 | 1   .5   .25   .125   .0625 |

FIG. 6

DETECTION OF WHEAT THAT HAS EXPERIENCED ELEVATED TEMPERATURES DURING THE GRAIN FILLING PERIOD

This application is a continuation of application Ser. No. 08/192,873, filed Feb. 7, 1994 now abandoned.

BACKGROUND OF THE INVENTION

1. Field of the Invention

The invention relates to methods to detect heat-stressed wheat, that is, wheat grain that has been exposed to elevated environmental temperatures during the grain filling period of wheat development. In particular, the invention relates to assays for measuring increased levels of wheat heat stress peptide present in the endosperm of heat-stressed wheat and methods to assess end-use properties of the grain from the measurement of wheat heat stress peptide. The present invention also relates to assay kits for carrying out the methods of the invention.

2. Description of the Related Art

The detrimental effect of elevated environmental temperatures on wheat grain during the growing season as assessed by changes in protein content of the grain has been recognized for a long time (Mangels, C. E., *Cereal Chemistry* 2:288–297, (1925)) and has continued to be of interest to cereal chemists over the years (Bequette, R. K., *Bulletin of the Association of Operative Millers*, pp. 5443–5450 (1989)). This problem has had increased significance as international trade of wheat grain and flour has increased. At times, an entire shipload or traincar of product is unsuitable for its intended end-use. This results from the inability to test and characterize grain that is a mixture of grain produced under a variety of environmental conditions. Two separate areas of research may be of interest. The first area relates to the response of an organism to a stress, for example, elevated environmental temperatures. This is denoted as the heat-shock response. In a second and separate area of technology, cereal chemists have correlated changes in the parameters used to evaluate wheat flour for bakery use with increased environmental temperature during the growing season.

In the first area of research, it is known that nearly all organisms respond in a remarkably uniform manner to an increase in temperature in excess of ten degrees over the normal environmental temperature for the organism (Nagao, R. T. et al., *Advances in Genetics* 28:235–274 (1990); Lindquist, S., *Annual Review of Biochemistry* 55:1151–1191 (1986)). This response is characterized by the initiation of increased synthesis of some proteins normally present in the cell at relatively low levels and the cessation of most other protein synthesis. Three distinct events result in this rapid change in metabolic activities with a cell: (1) there is increased transcription of the heat-shock proteins (hsp's) mRNAs, which are then preferentially translocated to the cytoplasm; (2) the transcription of most other mRNAs is suppressed; and (3) the normal translational activities of the ribosomes are disrupted so that hsp's are preferentially translated. The overall result of these events is that the cell rapidly begins synthesizing hsp's and synthesis of other peptides is repressed.

Although the number of hsp's induced by heat shock and their exact size are both tissue and species specific, five "universal" hsp's are found in all eukaryotes. Four of these are referred to by their apparent molecular weight on sodium dodecyl sulfate (SDS)-polyacrylamide gels: hsp 90, hsp 70, hsp 58 and the low molecular weight hsp 20–30. The fifth hsp is an 8 kD protein called ubiquitin. In eukaryotes each hsp is actually comprised of a multigene family, the members of which are regulated by different promoters and code for closely related protein isoforms (Lindquist, S., *Annual Review of Biochemistry* 55:1151–1191 (1986); Schlesinger, M. J., *Journal of Cell Biology* 103:321–325 (1986); Schlesinger, M. J., *Atlas of Science Biochemistry* 161–164 (1988)). Most of these hsp multigene families are synthesized at high levels in stressed cells. However, with the exception of the 72 kD protein, a highly inducible member of the hsp 70 family, all of these proteins are also present in much lower concentrations of unstressed cells. The initial observations that many hsp's are found in "normal" (unstressed) cells and that hsp 20–30 are developmentally induced in larval systems lead to the suggestion that hsp's play a role in normal cellular activities.

A technique frequently used to demonstrate hsp synthesis involves metabolic labeling wherein tissues are incubated with an amino acid tagged with a radioisotope (i.e. $^{35}$S, $^{14}$C, $^{3}$H). The tissue is then homogenized, and the proteins are separated by one or two dimensional electrophoresis, and autoradiographed to examine incorporation of the radioisotope into specific proteins. This technique provides information on the entire translational profile in response to a stress and is useful for identifying new inducible proteins. However, under continuous exposure to temperature stress some of these dramatic changes in translational patterns are transient (approximately six hours in wheat endosperm for the expression of the heat-shock proteins (Inwood, W. I. and Bernardin, J. E., *Plant Physiology* 93 No.1-Supp:88 (1990))). The short, transient response is followed by a rapid return to control levels of hsp synthesis (Heikkila, J. J., et al., *Journal of Biological Chemistry* 257:12000–12005 (1982); Canvalho, M., and Freitas, M. S., *Journal of Cell Physiology* 137:455–461 (1988); Lindquist, S., *Annual Review of Biochemistry* 55:1151–1191 (1986); Kapoor, M., *International Journal of Biochemistry* 18:15–29 (1986)). Heat-shock protein synthesis in wheat leaf tissue subjected to increased temperatures for an eight hour period demonstrated some of the hsp members accumulated sufficiently to visualize the proteins by silver staining electrophoresis gels (Vierling, R. A. and Nguyen, H. T., *Crop Science* 30:1337–1342 (1990); Zivy, M., *Theoretical and Applied Genetics* 74:209–213 (1987)). However, these proteins are degraded and revert to normal cellular levels within 24 hours following heat shock and are no longer detectable by silver staining.

Since the heat-shock genes are autoregulating, i.e. the gene product is not synthesized once it reaches a particular level in the cell, research has shown that detection of heat-shock protein synthesis must be carried out during the initial stages of heat-shock when the gene product is actively being synthesized. The autoregulatory level of these proteins in most cells is sufficiently low that an analysis of the cellular proteins by conventional protein staining techniques fails to detect the presence of the heat-shock protein. Recently, using immunometric assays, increased levels of heat-shock proteins in organisms have been detectable and used to evaluate chronic exposure of the organism to anthropogenic pollutants (U.S. Pat. No. 5,232,833). Under these conditions, increased levels of the heat-shock proteins are measurable during a short period following exposure to the pollutant providing there is continued exposure to low levels of the anthropogenic pollutant.

Beginning work by cell biologists in an attempt to understand the molecular mechanisms underlying the physiology of heat-stressed cells was reported by Welch, W. J. and Suhan, J. P., *Journal of Cell Biology* 103:2035–2053 (1986). Serious attention to this important cellular phenomena has occurred largely because of the discovery that all cells dramatically alter their gene expression in response to changes in environmental conditions. This alteration in transcriptional activity appears to be an attempt to protect the cell from damage and to repair existing damage. Collectively, the hsp's appear to be involved in the protection, enhanced survival, and restoration of normal cellular activities in stressed cells (Subject, J. R., Shyy, T.-T., *Cell Physiology* 19:C1–C17 (1986)). The protective cellular function of some hsp's is also suggested by the observation that a mild heat-shock enhances the tolerance of the cell to subsequent, more severe heat-shock, a phenomenon often referred to as thermotolerance. The induction, expression, and decay of thermotolerance correlates with the induction, accumulation, and degradation of heat-shock proteins (Nagao, R. T. et al., *Advances in Genetics* 28:235–274 (1990)).

The role of the hsp 70 and hsp 60 family of proteins in the cell is actively being researched, and members of both families have been demonstrated to play a role in the proper folding, oligomerization, and transport of newly synthesized proteins in cells (Hemmingsen, S. M., et al., *Nature* 333:330–333 (1988); Kozutsumi, Y., et al., *Nature* 332: 462–464 (1988); Chirico, W. J., et al., *Nature* 332:805–810 (1988); Beckman, R. P., et al., *Science* 248:850–854 (1990); Gething, M-J. and Sambrook, J., *Nature* 355:33–45 (1992); Miernyk, J. A., et al., *The Plant Cell* 4:821–829 (1992); Langer, T., et al., *Nature* 356:683–689 (1992); Craig, E. A., *Science* 260:1902–1904 (1993); Fontes, E. B. P., et.al., *The Plant Cell* 3:483–496 (1991); Li, X., et. al., *Science* 262:1054–1055 (1993)). Members of these families have also been identified as participants in the degradation of aberrant proteins in the cell (Kassenbrock, C. K., et al., *Nature* 333:90–93 (1988); Chaing, H-L, et al., *Science* 246:382–385 (1989)).

Accordingly, it would not have been expected that it would be possible to monitor previous exposure of an organism to elevated temperatures by measuring hsp levels after the initial transient hsp response. In most tissues and organisms, this is a transient response and the gene products, hsp's, do not accumulate in significant quantities nor are they retained in the cell at elevated levels for long periods of time.

The second area of background technology relates to the correlation of particular wheat dough properties with exposure of the grain to elevated temperatures during the growing season.

Many tests have been developed attempting to provide a means of assessing the quality of wheat flour and currently provide the baking industry with indicators of how a lot of bakery flour will perform in the bakery. These include measurements of dough strength, extensibility, mixing time, mixing tolerance, and loaf volume. However, breadmaking remains an art and not a science as there is not general agreement among cereal scientists which of these tests accurately predict baking performance. Wheat grain is usually sold for particular end-uses based on the variety.

Accurate field temperature data for wheat flour lots are not traditionally maintained in the production of a wheat crop. Therefore, when a correlation between the physical properties of a wheat dough and the environmental temperatures when protein was being synthesized in the developing wheat grain was suspected, the desired data was not available. Initial reports retrospectively correlated various dough properties with the number of hours above 35° C. in that geographical location during the period when grain filling was known to occur (Archer, M. J. and O'Brien, L., *Australian Journal of Agricultural Research* 38:465–471(1987); Blumenthal, C. S., et al., *Nature* 347:235 (1990); Blumenthal, C. S., et al., *Australian Journal of Agricultural Research* 42:21–30 (1991); Blumenthal, C. S., et al., *Australian Journal of Agricultural Research* 42:325–334 (1991)). Subsequent studies have increased the correlation between the phenomena, and experiments have been carried out using wheat flour that has been produced under carefully controlled environmental conditions (Blumenthal, C. S., et al., *Journal of Cereal Science* 18:3–21 (1993)).

Studies by Inwood and Bernardin, supra, have demonstrated that the heat-shock response in wheat endosperm tissue does not exactly parallel that found in other organisms nor in other tissues of the wheat plant. Synthesis of the storage proteins gliadin and glutenin of wheat endosperm are differentially affected by heat stress. The majority of protein synthesis in wheat endosperm tissue is suppressed as found in other organisms but the synthesis of the gliadin family of storage proteins remains at a "normal" level throughout the period of heat stress even continuing at temperatures of 45° C. (Inwood, W. I. and Bernardin, J. E., *Plant Physiology* 93 No. 1-Supp:88 (1990), Blumenthal, C. S., et al. *Australian Journal of Agricultural Research* 42:21–30 (1991)). This differential synthesis of gliadin versus glutenin proteins has been suggested as an explanation for the loss of baking performance. The synthesis of a 1550 molecular weight peptide whose synthesis is induced under heat-stress has been reported and its presence in flour has also been suggested to account for some of the changes observed in baking performance (Blumenthal, C. S., et al., *Australian Journal of Plant Physiology* 17:441–449 (1990)).

There is a need for a method to evaluate the effect of the temperature environment on wheat. In particular, what is needed is a technique that can evaluate the heat stress experienced by the wheat grain to monitor any adverse effect heat stress may have on the baking properties of the flour.

SUMMARY OF THE INVENTION

The invention provides methods to detect heat-stressed wheat, that is, wheat grain that has been exposed to elevated environmental temperatures during the grain filling period. The grain filling period is that period of wheat grain development following anthesis up to maturity of the grain. Grain maturity is reached when starch or protein is no longer being synthesized and dehydration of the grain is beginning.

Surprisingly, I have discovered that wheat heat stress peptide useful in my invention is synthesized when wheat grain is exposed to elevated temperatures during the grain filling period and that an increased level of wheat heat stress peptide persists in the wheat grain even after all protein synthesis has ceased, and the grain is in a dormant state, e.g., after harvest. This aspect of the invention serves as the basis for assays to determine whether wheat grain or flour has been exposed to elevated temperatures during the grain filling period. This is surprising because, as discussed above, the art teaches that heat-shock response is a short, transient response followed by a rapid return to constitutive levels of hsp synthesis.

In the method of the invention, wheat grain or flour is sampled, wheat heat stress peptide in the endosperm is extracted, and the level of wheat heat stress peptide is measured. Wheat grain or flour that has levels of wheat heat stress peptide two or more times greater than the constitutive level of this peptide in the wheat grain is determined to have been exposed to elevated temperatures during the grain filling period.

Another aspect of the invention is the use of the measurement of wheat heat stress peptide to assess end-use properties of wheat grain, e.g., dough properties, mixing and baking performance of the endosperm flour. This aspect encompasses methods for measuring the integrated exposure of wheat grain to increased temperature levels during the grain filling period, and methods of assessing end-use properties from the measurement of wheat heat stress peptide.

Another important aspect of the invention is the provision of sensitive, rapid, and specific methods to measure wheat heat stress peptide. Such immunoassays include, for example, single or double antibody assays or assays using antibody to measure wheat heat stress peptide complexed with adenosine triphosphate (ATP).

Another aspect of the invention is the provision of a method to prepare antibodies for the assay of wheat heat stress peptide.

Still another aspect of the invention are kits for measuring wheat heat stress peptide to detect wheat grain that has been exposed to elevated temperatures during the grain filling period or to measure end-use properties.

With the method and kits of the present invention, it will not be necessary to have an experienced laboratory technician interpret test results. It is also possible to utilize as the measuring method a rapid sandwich immunoassay employing, for example, a dipstick format for the routine and rapid analysis of a large number of samples. The use of monoclonal antibodies can ensure an almost infinite supply of a standard reagent for consistent results.

Further, the invention provides a simple and inexpensive technique suitable for field use that can specifically measure the integrated heat stress experienced by the wheat grain during grain filling and thereby monitor any adverse effect this heat stress has on the end-use properties of the flour.

Other objects and advantages of the present invention will become readily apparent from the ensuing description.

DETAILED DESCRIPTION OF THE INVENTION

The present invention provides methods for detecting wheat grain that has been exposed to elevated environmental temperatures during the grain filling period. I have surprisingly discovered that wheat heat stress peptide is synthesized when wheat grain is exposed to elevated environmental temperatures during the grain filling period and that an increased level of wheat heat stress peptide persists in the wheat grain even after harvest. For purposes of this invention, the term "wheat heat stress peptide" is defined to mean a member of the hsp 70 family in wheat that is produced in the wheat grain endosperm in response to heat stress during the grain filling period and which persists at levels greater than constitutive when the grain is in the dormant state. Initiation of the synthesis of wheat heat stress peptide generally begins at environmental temperatures of about 30°–32° C. I have found that rapid synthesis of wheat heat stress peptide is occurring at 35° C. For purposes of this invention, the term "elevated environmental temperatures" means temperatures in the environment of the wheat grain that cause the production of wheat heat stress peptide at greater levels than constitutive. Wheat heat stress peptide in a wheat variety can be isolated from immature or mature wheat grains and identified by comparing the protein profile of wheat that has been grown at elevated temperatures during the wheat filling period with the same wheat variety that has not been exposed to elevated temperatures during the grain filling period. This is described in detail in Example 1, below.

Wheat heat stress peptide is further characterized as follows: it has an isoelectric point in the range of 5.3–7.7 and a molecular weight in the range of 68–79 kD. Example 1, below, describes isolation, purification, and characterization of wheat heat stress peptide produced in *Triticum aestivum*, var. Vulcan in response to elevated environmental temperatures. The peptide has an isoelectric point of 7.1±0.1 as determined by the experimental conditions set forth in Example 1, and a molecular weight of 77±2 kD as determined by the experimental conditions set forth in Example 1. Also, as discussed in detail in Example 1, the peptide reacts with antibodies to an epitope equivalent to that between amino acids 504–617 of human hsp 70.

The method to detect wheat that has been exposed to elevated temperatures during the grain filling period comprises the following steps:

1. Obtaining a test sample. The wheat heat stress peptide of the invention is produced in the endosperm of the wheat grain. Thus, the test sample is selected to contain wheat endosperm. Exemplary of such samples are mature or immature wheat grain, or flour prepared from endosperm or from whole grain. The sample can consist of mixed varieties of wheat.

One aspect of the invention is the ability to detect bulk lots, e.g., traincars, of wheat that have been heat-stressed. To obtain a measure of heat stress representative of the bulk lot, a representative sample is obtained. By "representative sample" is meant a sufficiently large sample that by standard statistical analysis the data obtained from the sample would be representative of the larger bulk lot.

2. Extraction of wheat heat stress peptide. The test sample is treated so that the cellular contents of the endosperm cells are accessible to extractant. The test sample is extracted until at least two or more times the constitutive level of wheat heat stress peptide, if present, is extracted. Where knowledge of the total amount of wheat heat stress peptide is desired, disruption of the endosperm cells and extraction are carried out so as to extract substantially all of the wheat heat stress peptide. These procedures are described in detail below. By "constitutive level" is meant the amount of wheat heat stress peptide that occurs in wheat grain that has not been heat-stressed, that is, that has not been exposed to elevated temperatures during the grain filling period. I have found that the constitutive level of wheat heat stress peptide has a range of 60 to 89 µg per gram of flour for five varieties of wheat. The average is 70 µg per gram flour.

Techniques to disrupt endosperm cells to make the cellular contents accessible to extractant are known to those in the art. Techniques useful to disrupt the endosperm cells of mature wheat include (1) grinding in a mortar with pestle; (2) ball mills; (3) any of the standard milling machines used in the flour milling industry. Immature grain may be extracted after the tissue is ground in the extraction solution in (1) a blender or similar apparatus; (2) a Polytron homogenizer or similar equipment; (3) grinding in a mortar with pestle; or any apparatus where the endosperm cells are ruptured. It is preferred that the sample after treatment have an average particle size of less than 50 microns to ensure that the majority of all endosperm cells are broken and the cellular contents accessible to extractant. Since flour is normally less than 50 microns, no disruption treatment is generally required.

Extractants are aqueous and buffer solutions suitable for extraction of peptides. These are well known in the art. These may include additives to increase extraction of endosperm proteins, e.g., SDS. An example of a mild extractant is: 0.1 M TRIS.HCl (pH 8.0), 100 mM KCl, 50 mM magnesium acetate, 1 mM dithiothreitol. Also effective are stronger extractants such as 0.063M TRIS.HCl (pH 6.8), 2% SDS, 5% β mercaptoethanol, 10% glycerol. Protease inhibitors are included in buffers used for cell or tissue disruption.

Where extraction of substantially all of the wheat heat stress peptide is desired, multiple extractions or continuous extraction is carried out until wheat heat stress peptide is not detected.

3. Measurement of wheat heat stress peptide. Exemplary ways to measure the level of wheat heat stress peptide in the sample include immunoassays or isotopic labelling techniques. Exemplary immunoassays include the following: (1) the extracted peptide can be incubated in the wells of microtiter plates containing immobilized antibody, immobilized ATP or any reagent which selectively binds wheat heat stress peptide to bind the peptide to the immobilized reagent. The bound wheat heat stress peptide is reacted with an immunologic binding partner capable of binding to the bound wheat heat stress peptide and detecting the binding partner, for example, a secondary antibody. This detection system can be an enzyme (e.g., alkaline phosphatase) conjugated to the secondary antibody to produce a color reactant whose concentration will be proportional to the amount of a particular stress peptide; (2) the peptide can be concentrated by ATP affinity columns and the concentrated heat stress peptide immobilized on nitrocellulose. The concentration can then be measured by an antigen-antibody reaction using an alkaline phosphatase conjugated antibody; (3) either monoclonal or polyclonal antibodies, immobilized ATP, or another reagent that specifically binds the heat stress peptide, may be employed as part of a sandwich or competitive enzyme-linked immunosorbant assay (ELISA). In this procedure, the purified antibody is labeled by attaching an enzyme that can react with a colorless substrate to give a colored product. The amount of colored product released in a fixed period of time depends on the concentration of enzyme, and this is also a measure of the amount of antibody present. The antibody in turn will bind in proportion to the amount of stress peptide (antigen) that is present. The amount of colored product produced in the reaction is therefore a measure of the amount of heat stress protein present. The intensity of the colored product can be quickly and conveniently compared with the color of other standard solutions containing unstressed wheat cell extracts and varying amounts of wheat heat stress peptide; (4) in a representative sandwich ELISA, purified heat stress peptide antibody is placed in the wells of microtiter plates in order to immobilize it to the plastic surface; i.e., solid carrier. Cells or small amounts of tissue containing the heat stress peptide are disrupted and placed in the wells of the microtiter plates to allow the antigen to attach to the immobilized antibody. The cell/tissue extract is removed, the wells are washed, and a second antibody that is labeled with enzyme is placed in the well. The excess antibody remaining unbound to the immobilized antigen is then removed and the color-producing reaction is initiated by the addition of the enzyme substrate.

4. Comparison of the level of wheat heat stress peptide in the test sample to constitutive levels. To determine if the test sample has been exposed to elevated temperatures during the grain filling period, the level measured in step 3 is compared to the level of wheat heat stress peptide that is present in wheat that has not been exposed to elevated temperatures during the grain filling period (the constitutive (base-line or control level)). For measurement of the normal level of this peptide in non-stressed grain, samples should be collected in such a manner as to not inadvertently activate the heat shock protein response. Proper handling procedures would include ensuring that the sample is not exposed to elevated temperatures before collection. Measurement of the control is carried out as described for the test sample or comparison is made to a previously obtained value for constitutive level of wheat heat stress protein. If the level of heat stress peptide in the test sample is two or more times greater than the constitutive level, the test sample is determined to have been exposed to elevated temperatures during the grain filling period. Where the sample consists of mixed varieties of wheat, the sample is determined to be exposed to elevated temperatures during the grain filling temperature if accumulated concentration in the mixed sample is two or more times greater than a baseline concentration for average non-heat stressed samples of similar varieties.

Figure 4:
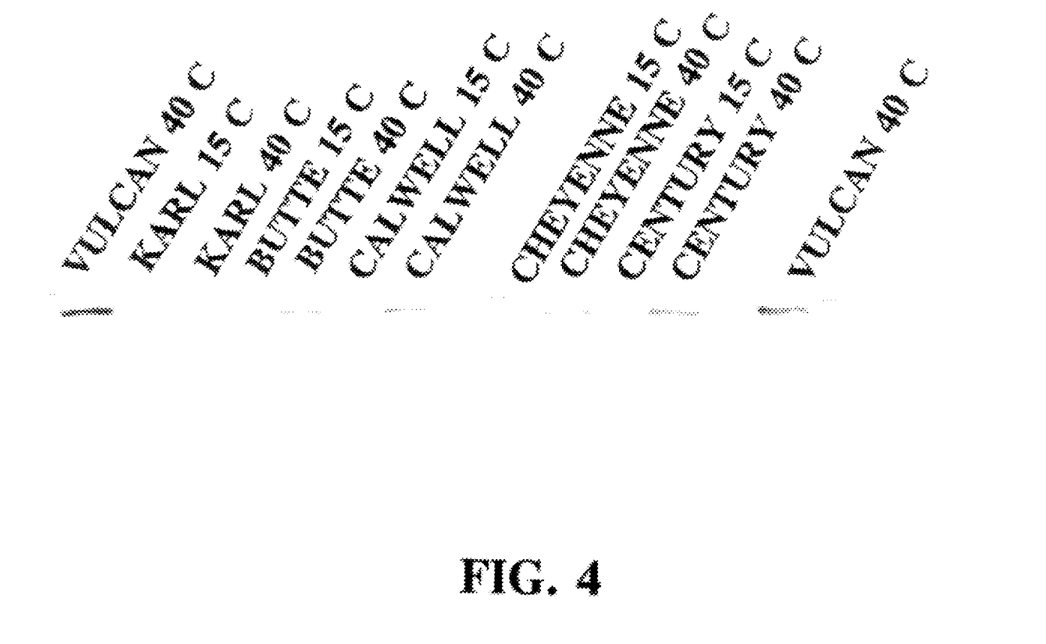
FIG. 4 is a Western blot of heat-stressed wheat representing several different varieties and all the major wheat classes that had experienced elevated temperatures during grain filling and the corresponding levels for heat stress peptide in the same varieties grown under optimal growth conditions.

Example 2, below, illustrates in detail the method of the invention to detect heat stressed wheat. As shown in FIG. 4 (Example 3), the method is useful to detect heat stress in different wheat varieties and classes.

Another aspect of the invention are methods to produce antibodies useful to detect and measure wheat heat stress peptide.

The preparation of hybridoma cell lines can be done by techniques which are well known to those skilled in the art. (See, for example, G. Kohler and C. Milstein, 1975, *European Journal of Immunology* 6:511–519 (1976); Koprowski, et al., U.S. Pat. No. 4,196,265, and Wands, U.S. Pat. No. 4,271,145; *Antibodies, A Laboratory Manual*, Ed Harlow and David Lane, Cold Spring Harbor Laboratory (1988), all of which are herein incorporated by reference.)

The method of preparing the hybridomas comprises the following steps:

Immunization. Two strains of mice, five mice each are inoculated with a solution of purified wheat heat stress peptide (10 μg to 100 μg) emulsified in complete Freund's adjuvant. A series of inoculations at three week intervals will elicit a good antibody response.

Production of Hybrid Cells. Cell fusion techniques, selection procedures, and methods for growth of hybridomas are known to those skilled in the art. In one effective cell fusion procedure, poly(ethylene glycol) (PEG) is used in the fusion step, and hypoxanthine-aminopterin-thymidine (HAT) is used in the selective medium.

Analysis of Hybridomas. The growing colonies are tested for the presence of antibodies that recognize the wheat heat stress peptide. Standard assay methodology and widely used commercial reagents, such as goat anti-mouse immunoglobulin G (IgG) antibodies conjugated to alkaline phosphatase, can be used to reveal the presence of antibody in the culture supernatants.

Cloning of Hybridomas. Hybridomas which are positive for the desired antibody production are cloned as they are detected. Cloning can be accomplished by any method known in the art. The cloning procedure can be repeated as needed. Antibody-secreting hybridomas can be grown in a variety of vessels, in devices such as hollow fibers, or within a host animal.

Systematic Screening of Clones. To obtain the monoclonal antibodies, systematic screening is carried out. A preliminary screening of the supernatant culture fluid from the cloned hybridomas of interest is screened to confirm the presence of antibodies that recognize the antigenic determinants of wheat heat stress peptide. This can be accomplished using plastic assay wells coated with wheat heat stress peptide. To screen for antibodies having a high affinity for wheat heat stress peptide an inhibition ELISA is conducted. An antibody concentration is selected to give 50 to 100% of maximal binding to a wheat heat stress peptide-coated assay well. Antibody is mixed with a range of concentrations of wheat heat stress peptide, incubated, and applied to the assay plate. The plate is then incubated, washed, and developed as for the direct binding assay. Antibodies are selected which are at least 90% inhibited from binding to the solid phase by wheat heat stress peptide at less than 100 ng/ml.

The invention also encompasses kits for carrying out the methods of the invention, in which antibody, substrate, optionally washing solution, and detection system and standards are supplied in separate containers, as appropriate, or coated on solid phases. The surface could be a plastic assay dish, a bead, or hollow fiber, for example. Reagents may be provided in solid or liquid form. The assay could also be arranged as a qualitative assay—such as might be used in a quality control application. In such a format, the appropriate reagents would be coated on surfaces and supplied in solutions at concentrations which would reveal a positive assay if more than a predetermined minimum of wheat heat shock protein were present in the sample.

The kit could be a "dipstick" containing the appropriate binding reagents, competitors, and antibodies and colored indicator allowing the result to be displayed in a window on the dipstick indicating a heat-stressed wheat sample.

The procedures for analysis of heat stress peptide-containing samples can be readily automated, for example by provision of automatic pipeting equipment and automated ELISA reader and computer.

Another aspect of the invention is the use of the measurement of wheat heat stress peptide levels to assess end-use properties of wheat grain. End-use properties include dough properties as measured by mixograph, farinograph, extensigraph, and other standard physical wheat flour tests used by cereal chemists to measure rheological properties of dough or flour slurries; baking performance of the endosperm flour to make white bread, whole grain breads, hamburger buns as well as other specialty rolls; the production of extruded products such as breakfast cereals as well as pasta products and noodles.

The method to assess end-use properties from the measurement of wheat heat stress peptide comprises the following steps:

1. Measuring the integrated exposure of wheat grain to elevated temperatures during the grain filling period by carrying out steps 1–3 on the test sample as described above.

2. Comparing the value to a calibration curve that correlates the level of wheat heat stress peptide and the end-use property being assessed.

3. Based on the comparison, determining whether the test sample is suitable for the end-use property being assessed.

As used herein, "standard physical wheat flour tests" means those tests approved for use by cereal chemists for testing the physical properties of wheat flour doughs, flour slurries or other wheat flour mixtures and for measuring the potential use of wheat endosperm flour or whole grain in any product that provides specific physical properties to the product as a result of the presence of the wheat endosperm proteins, e.g., thickeners, bread dough, pasta dough.

This aspect encompasses methods for measuring the integrated exposure of wheat grain to elevated temperatures during the grain filling period. By "integrated exposure" is meant the total time the grain is exposed to elevated temperatures from immediately following anthesis to grain maturity even though there may be periods of several days between elevated temperature episodes where an elevated temperature is never reached.

Further, the invention provides a simple and inexpensive technique suitable for field use that can specifically measure the integrated heat stress experienced by the wheat grain during grain filling and thereby monitor any adverse effect this heat stress has on the end-use properties of the flour.

Example 4 shows the correlation of the level of wheat heat stress peptide in the correlation with mixograph time and mixograph tolerance for several wheat samples experiencing four days of heat stress. Longer periods, e.g., 20–30 days of heat stress as described in Example 3, result in the complete inability to develop a dough. The mixograph therefore shows infinite mixograph time and zero tolerance.

Accordingly, the level of wheat heat stress peptide as measured in Example 2 provides a direct measure of the utility of the wheat flour end-use.

EXAMPLES

The following examples are intended only to further illustrate the invention and are not intended to limit the scope of the invention which is described by the claims.

Example 1

This example describes the purification and characterization of wheat heat stress peptide.

Wheat, variety Vulcan, was maintained under normal growth conditions (18° C. night, 25° C. day) in the greenhouse. It was stressed by placing the plants in a growth chamber maintained at 40° C. and 50% relative humidity when a majority of the wheat heads on the plants were 10 to 15 days post anthesis.

Figure 1:
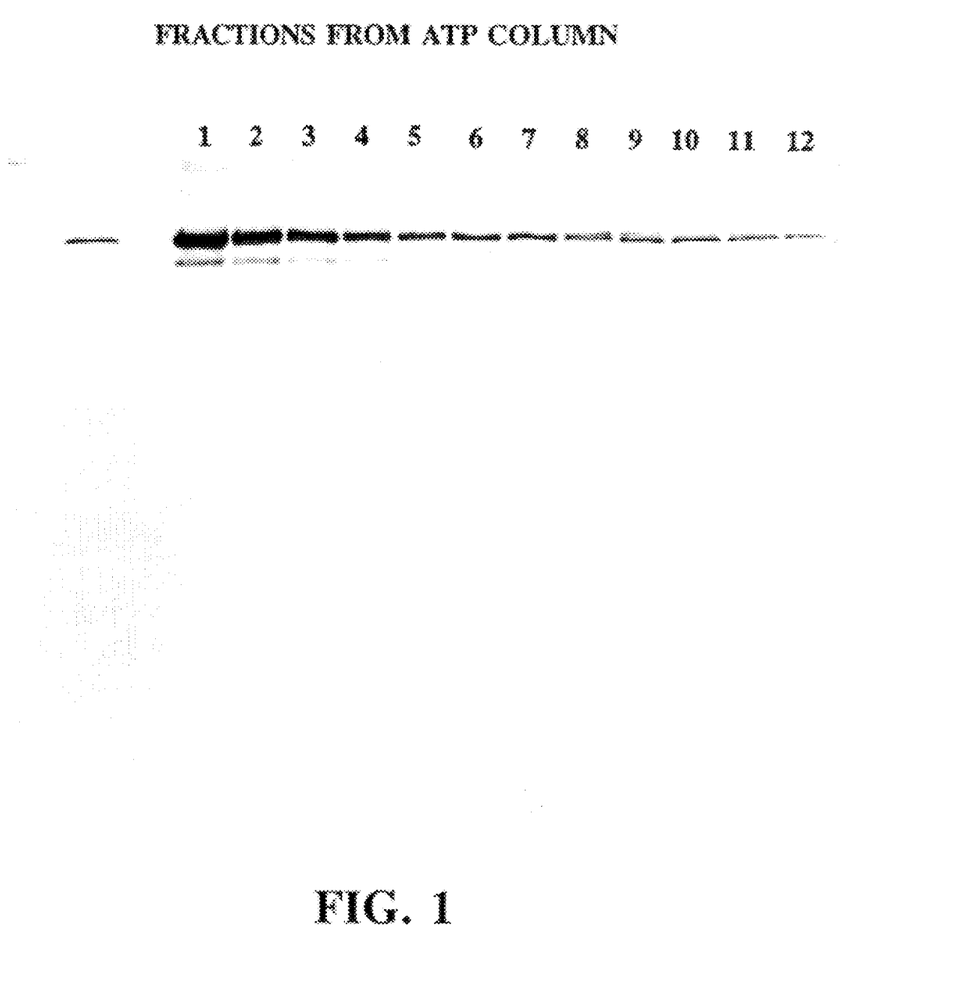
FIG. 1 shows a Western blot of affinity-purified wheat heat stress peptide from heat-stressed wheat var. Karl.
Figure 2:
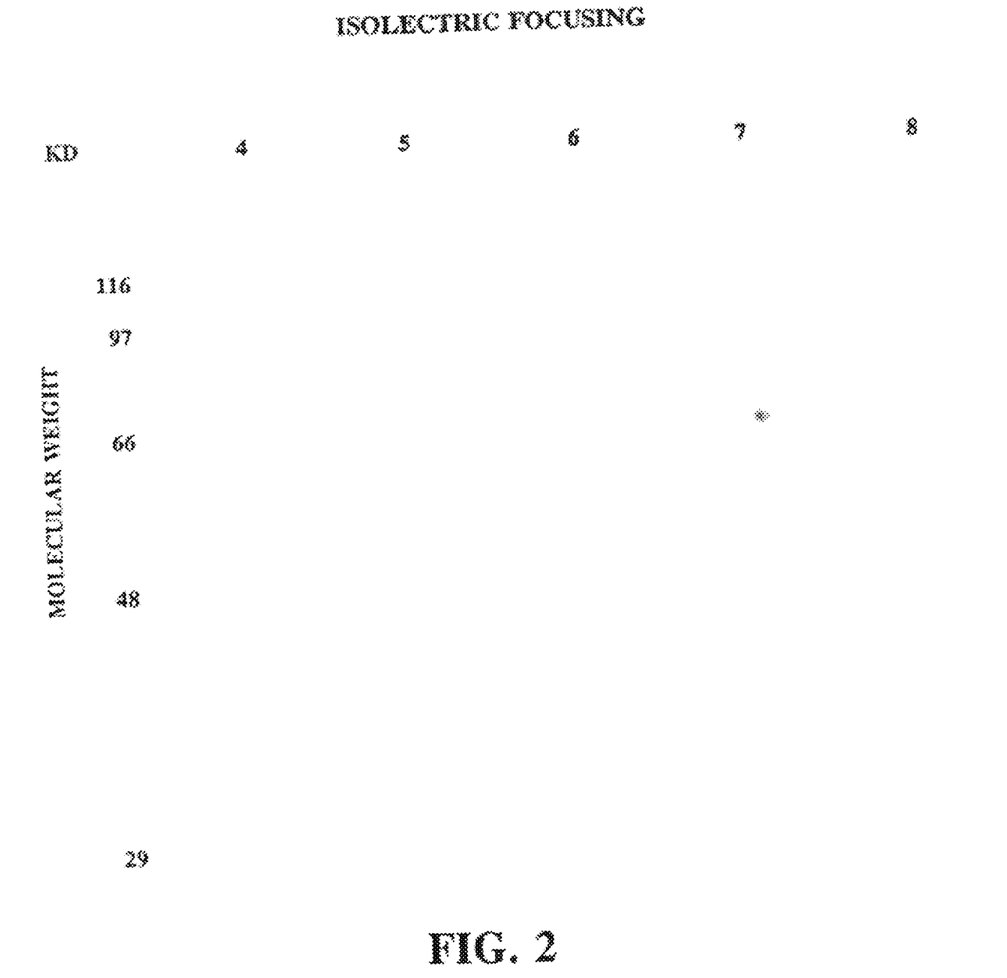
FIG. 2 is a Western blot two dimensional analysis of purified heat stress peptide defining the molecular weight and isoelectric point for wheat heat stress peptide.

Four hours after the introduction of the heat stress, the developing grains were harvested by removing them from the head, cutting the developing embryo from the grain, and the endosperm expressed by squeezing from the end of the grain opposite the removed embryo. The endosperm was homogenized by a tissue homogenizer, Polytron, with a P10 generator, in an aqueous buffer (0.1M TRIS.HCl (pH 8.0), 0.10M KCl, 0.050M magnesium acetate, 0.001M dithiothreitol, 0.001M phenylmethylsulfonyl fluoride). The sample slurry was then centrifuged at 12,000×g. The supernatant was removed, transferred to another centrifuge tube, and centrifuged at 128,000×g. The wheat heat stress peptide was concentrated from this solution using an ATP affinity column as described by Giorini and Gallili in *Theoretical and Applied Genetics* 82:615–620 (1991) which is incorporated herein by reference. Further purification of the wheat heat stress peptide was accomplished by the procedure of Welch and Feramisco in *Molecular and Cell Biology* 5:1229–1237 (1985) which is incorporated herein by reference, and its purification was monitored by Western Blotting using monoclonal antibodies elicited against human heat shock protein 70, (MA3-006, from clone 3a3, sold by Affinity BioReagents, Inc.). Homogeneity of the peptide was assessed by sodium dodecyl sulfate polyacrylamide gel electrophoresis (SDS-PAGE). FIG. 1 shows a Western blot of affinity purified wheat heat stress peptide examined by SDS-PAGE. To confirm that the purified peptides are those specifically induced by increased environmental temperature, comparative two dimensional PAGE was performed with purified peptide from unstressed and stressed wheat endosperm cell extracts labeled with $^{35}$S labeled methionine. The details of this labeling are well known to those experienced in the art. FIG. 2 shows a two dimensional sodium dodecyl sulfate-isoelectric focusing (SDS-IEF) analysis for the affinity purified wheat endosperm heat stress peptide.

Example 2

The following example describes measurement of wheat heat stress peptide to detect wheat grain that had been exposed to elevated temperatures during the grain filling period.

Wheat plants, variety Vulcan, were grown in the greenhouse programmed to provide 18° C. night and 25° C. day temperatures. At varying times after the plants had gone through anthesis, the plants were placed in a growth chamber programmed to provide 18° C. night and 40° C. day temperatures. The plants remained in the growth chamber three days and were then returned to the greenhouse. The plants remained in the greenhouse until the grain was mature. Grain from wheat heads that received the three day heat stress beginning 1, 11, 21, and 31 days after anthesis were treated as follows:

1. The germ was removed from the grain and the grains were weighed (3 grains).

2. The grains were ground to a fine powder in a mortar with pestle and a 100 mg sample was taken for analysis. This sample condition is equivalent to flour. Therefore, if flour is available, the 100 mg sample is taken from the bulk flour. Less material can be used as the amount required for the assay is 0.0003 gm flour but to ensure sampling is representative, we typically use 100 mg.

3. This ground tissue was extracted with 15× volumes of extraction buffer A at room temperature for 5 minutes and centrifuged to remove insoluble material. (Buffer A:0.1M TRIS.HCl (pH 8.0), 0.10M KCl, 0.050M magnesium acetate, 0.001M dithiothreitol, 0.001M phenylmethylsulfonyl fluoride), and the samples centrifuged at 12,000×g and 128,000×g.

4. 200 µl of the supernatant were applied to a chromatography column containing 1 ml agarose beads with ATP covalently attached.

5. The column was washed with a low salt buffer (1.5 ml) and then a high salt buffer (1.5 ml) to remove any protein that was not affinity bound to the ATP (unbound peptides). Low Salt Buffer: 0.02M TRIS acetate (pH 7.5), 0.10M NaCl, 0.001M ethylenediaminetetraacetic acid, 0.015M β mercaptoethanol, 0.003 M MgCl. High Salt Buffer: Low Salt Buffer with NaCl concentration equal to 0.02M.

6. The column was then eluted with three 500 µl washes of Low Salt Buffer containing 3 mM ATP. This eluted the bound heat stress peptide in a buffer that could be applied to the slot or dot blot apparatus. A 12 µl fraction of the eluate was also used in an electrophoresis experiment where the sample was separated by molecular weight. The separated proteins were then transferred to a membrane for detection and quantitation by an antibody containing a reporter element.

7. For the dot blot, 20 µl aliquots were applied to a MSI NitroPlus membrane which absorbed the protein directly from the eluate. The membrane was then reacted with the antibody containing the alkaline phosphatase reporter element. Also applied to the dot blot apparatus was a series of concentrations of purified heat stress protein isolated from Vulcan wheat. Since all wheat varieties tested produce the same epitope containing protein in response to heat stress, any variety can be used to produce the standard heat stress protein used in developing the standard curve to quantitate the level of heat stress protein in the unknown.

8. The slots were rinsed with 200 µl of buffer C, 2X. Buffer C:0.01M TRIS.HCl (pH 6.8).

9. The membrane was next reacted with 5% non-fat dry milk in phosphate buffered saline solution to block reactive sites on the membrane that do not contain protein.

10. The membrane was next reacted with 3 µl MA3-006 antibody in ascites fluid diluted in 15 ml phosphate buffered saline containing 5% non-fat dry milk.

11. The membrane was rinsed 3X with phosphate buffered saline.

12. The membrane was rinsed with TRIS buffered saline.

13. The membrane was reacted with 3 µl goat-anti-mouse antibody conjugated with alkaline phosphatase.

14. The membrane was rinsed 4X with TRIS buffered saline.

15. The membrane was reacted with stabilized alkaline phosphatase substrate overnight to allow full development of the sample.

16. The membrane was dried in warm air.

17. The dot images on the membrane were quantitated in a densitometer and the value compared with the standard curve to establish the level of the protein containing the heat stress epitope in the unknown sample.

Figure 3:
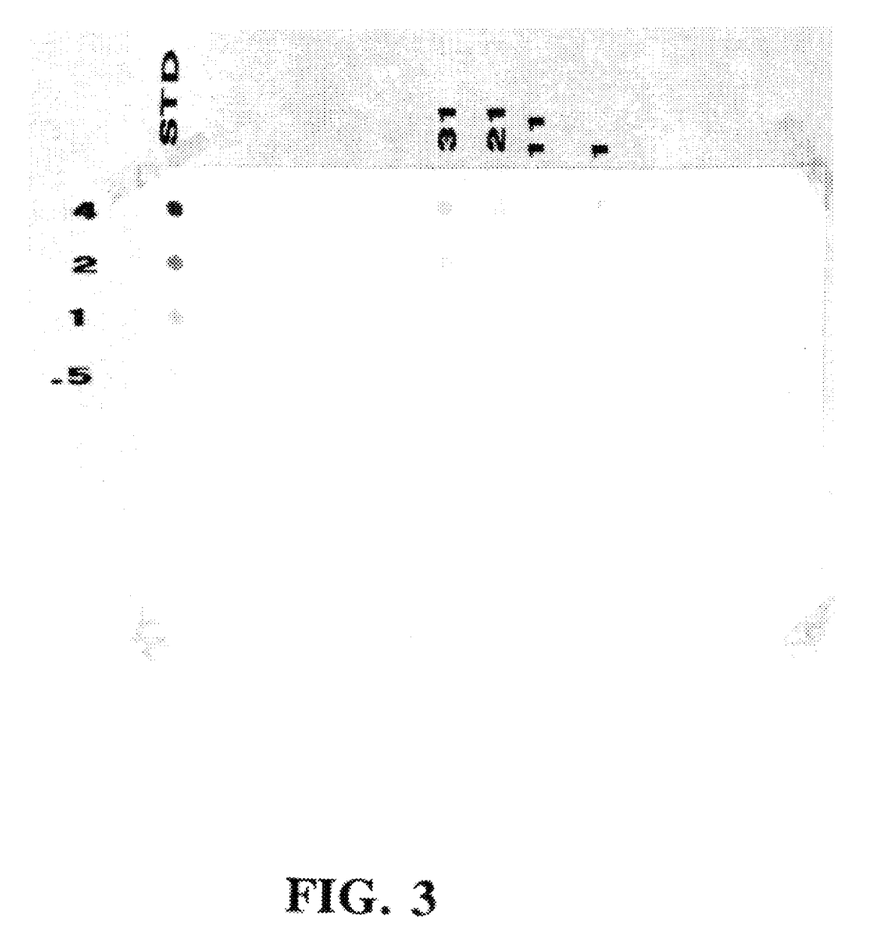
FIG. 3 shows a dot blot consisting of a set of standards and 4 samples of heat-stressed wheat that was exposed to elevated temperature for three days at varying times after anthesis.

The results are shown in FIG. 3. Quantitation of the intensity of the dot samples compared with those of the purified heat stress peptide standards provides a measurement of the level of heat stress peptide in the unknown samples.

Example 3

The following example describes the uniformity of the heat stress peptide expression for five major wheat classes represented by widely grown varieties.

Wheat classes: Hard Red Winter Wheat, vars. Karl, Arapahoe, Cheyenne and Century; Hard Red Spring Wheat, var. Butte; Soft Red Winter Wheat, var. Caldwell. Durum Wheat. var. Monroe; Hard White Winter Wheat, var. Vulcan, were assayed for production of the heat stress peptide following heat stress. Mature grain was harvested that had been exposed to heat stress for six hours per day throughout the grain filling period. Heat stress peptide was extracted with the SDS extraction buffer (0.063M TRIS.HCL (pH 6.8) 2% SDS, 5% β mercaptoethanol. 10% glycerol) from the ground grain (100 mg grain with the embryo removed was extracted with 4 ml extraction buffer). Following centrifugation at 12.000×g. the supernatant from this extraction was examined by SDS PAGE (12 µl aliquots were applied to each lane) and the completed electrophoresis was followed by Western Blotting and development with the MA3-006 antibody conjugated to alkaline phosphatase as described in Example 2. FIG. 4 shows the results obtained from the varieties Karl, Cheyenne, Butte, Caldwell, Century and Vulcan. The Vulcan sample for this experiment was heat stressed for only three hours and the heat stress peptide immediately extracted.

Example 4

The following example describes the detection of heat stress peptide in field grown wheat and greenhouse grown wheat that experienced heat stress for three days between 10 to 14 days following anthesis.

Heat treatment in the greenhouse: Transparent compartments were used as heating chambers. This method of spike heating was developed by C. F. Jenner (*Australian Journal of Plant Physiology* 18:165–177 (1991)).

The heat treatments consisted of night temperatures of 25° C. and day temperatures of 38° C. These temperatures were maintained by manually switching the temperature differential between ambient and treated for the day and night and maintaining the ambient temperature monitor in a large insulated sand container which served as a heat reservoir. Generally, the temperature varied only ±1° C. in the heater boxes during the experiment. Each heating chamber was at the same temperature (differential 1–2° C.) and as control, plants were left under normal greenhouse conditions where the temperature was held between 18° C. and 25° C. The heat treatment duration was 6 hours 38° C., 12 hrs. 25° C., 12 hrs. 38° C., 12 hrs. 25° C., 12 hrs. 38° C., 12 hrs. 25° C., 12 hrs. 38° C., 12 hrs. 25° C., 6 hrs. 38° C., and then returned to ambient conditions.

The heat treatments were started at 13–14 days after anthesis. The spikes from the main tillers of each plant were randomly inserted through a slit into the two heating chambers. All the other tillers per plant were cut and discarded. Immediately after the treatments the spikes were sampled by taking every other grain, taking four grains from every spike, or harvesting grain from the top halves of the spikes. The unsampled grains were left to mature and dry on the spike before being harvested and weighed.

Heat treatment in the field: Glass flasks were used as heating chambers with an insulating air bubble, aluminum backed sheet wrapped around the sides of the flasks. Poles were put into the ground and the flasks tied to the poles at head height. A few heads (30–75) were inserted into the flasks and tied together and to the pole. Thermocouples were put into two of the flasks, one in the ground and one thermocouple at head height to record the temperatures 24 hours a day. The plants were covered with these flasks for 96 hours continuously. The flasks were set up at 10:00 AM and removed at 10 AM four days later. The experiment consisted of four replications with two flasks per replication.

Once the grain had fully matured, grain samples were harvested and milled in a Quadramat Junior mill. Flour samples were then evaluated in a mixograph using standard Cereal Chemistry Procedure 54–40A (*American Association of Cereal Chemists' Approved Methods* (51993)) providing Mixograph time and Mixograph tolerance data. The level of heat stress peptide in these samples was evaluated using the dot blot quantitation assay as described in Example 2. The data are presented in Table 1.

The data show the correlation between Mixograph time and Mixograph tolerance and the level of heat stress peptide for two varieties of wheat grown under controlled greenhouse conditions as well as data for the same two varieties of wheat grown under field conditions where the environmental temperature during grain filling was known.

Figure 5:
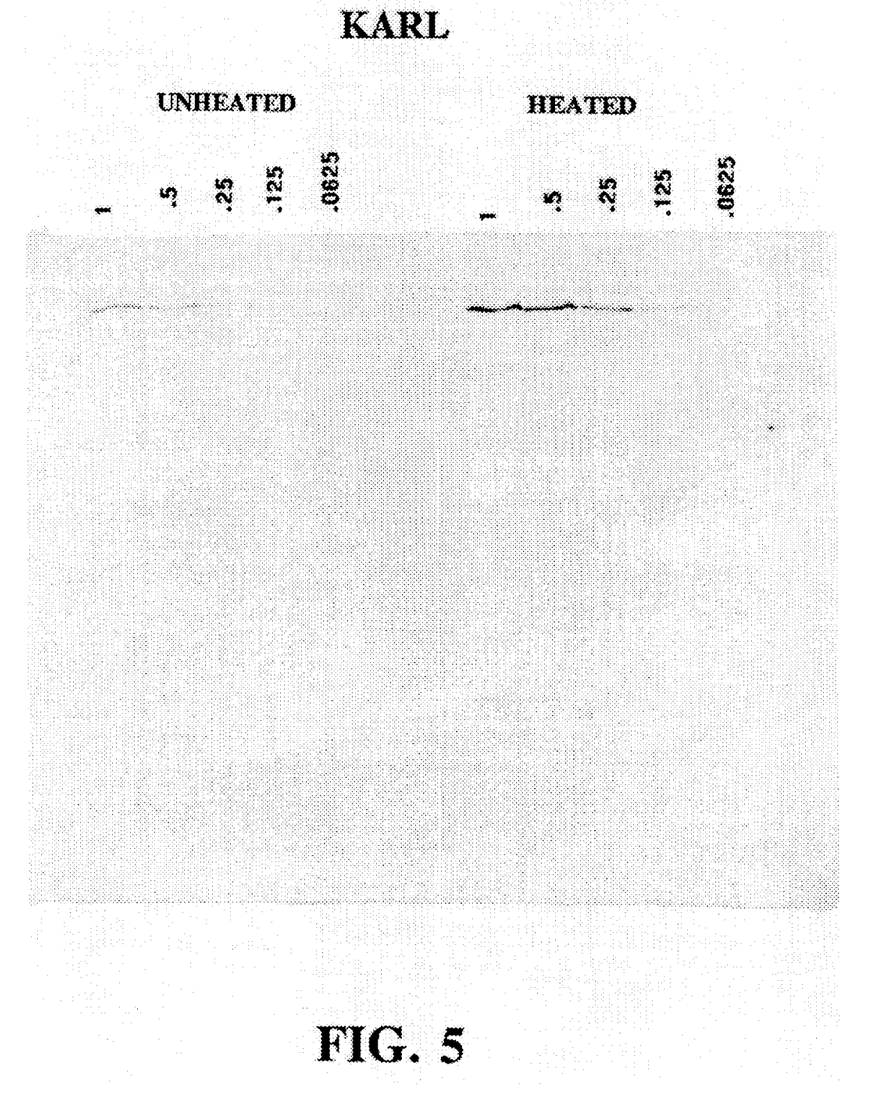
FIG. 5 is a Western blot dilution series for wheat, var. Karl, exposed to a three day heat stress during grain filling. The data establishes the linearity of the reaction of the monoclonal antibody with the levels of wheat heat stress peptide.
Figure 6:
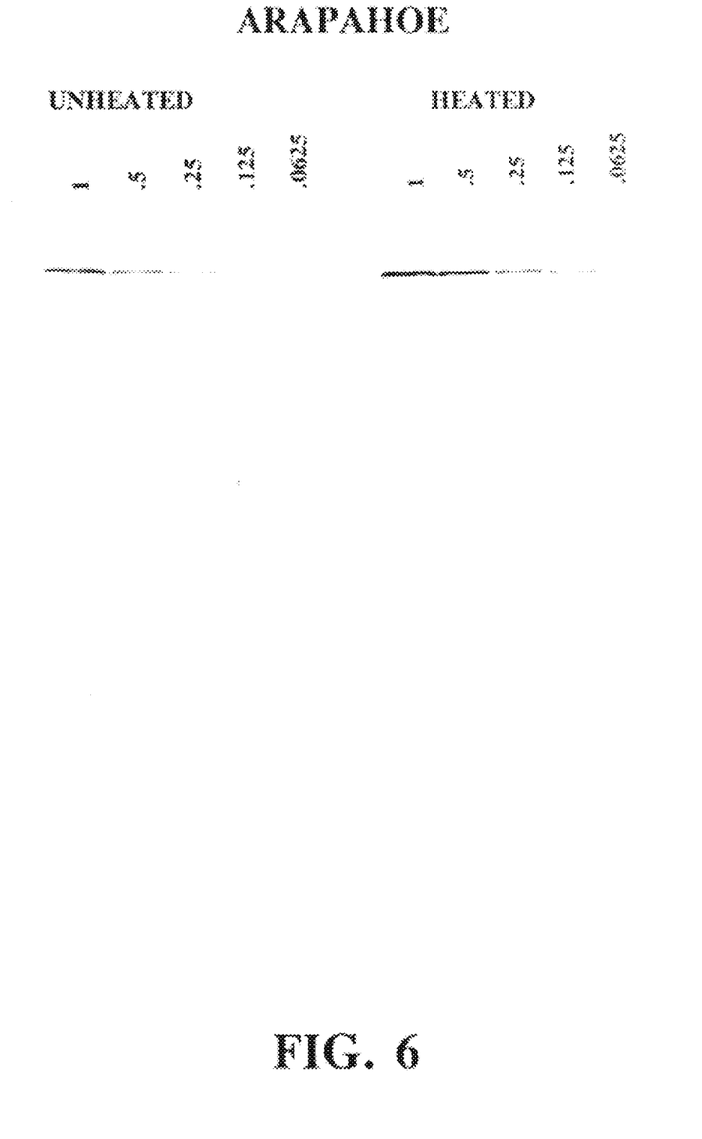
FIG. 6 is a Western blot dilution series for wheat, var. Arapahoe, exposed to a three day heat stress during grain filling. The data establishes the linearity of the reaction of the monoclonal antibody with the levels of wheat heat stress peptide.

To be sure there was a linear reaction between the level of heat stress peptide and the antibody, dilution series of two of these flours were prepared and examined by an SDS-PAGE and Western blot analysis. FIGS. 5 and 6 show these Western blots. The data establishes the linearity of the monoclonal antibody with the levels of wheat heat stress peptide.

TABLE 1

| | KARL | | ARAPAHOE | | CHEYENNE | |
|---|---|---|---|---|---|---|
| VARIABLE | HEATED | NO HEAT | HEATED | NO HEAT | HEATED | NO HEAT |
| FLOUR YIELD (%) | 66.77 | 70.18 | 66.20 | 68.37 | N/A | N/A |
| GRAIN WEIGHT (mg) | 27.61 | 29.93 | 25.28 | 30.08 | 21.7 | 37.0 |
| PROTEIN FLOUR (%) | 13.97 | 11.90 | 15.30 | 13.65 | N/A | N/A |
| PROTEIN/ GRAIN (mg) | 3.86 | 3.56 | 3.12 | 3.77 | N/A | N/A |
| MIXOGRAPH TIME (min) | 3.2 | 3.6 | 3.12 | 3.77 | INFINITE | 3.9 |
| MIXOGRAPH TOLERANCE | 3.5 | 3.0 | 4.5 | 4.07 | 0.00 | 4.2 |
| HEAT STRESS PEPTIDE (µg/g) | 208 | 62 | 97 | 42 | 694 | 60 |

It is understood that the foregoing detailed description is given merely by way of illustration and that modification and variations may be made therein without departing from the spirit and scope of the invention.

I claim:

1. A method for detecting wheat grain that has been exposed to elevated temperatures during the grain filling period, which comprises:
   (a) obtaining an endosperm-containing sample of mature wheat grain, said wheat endosperm having a constitutive level of wheat heat stress peptide when not exposed to elevated temperatures during the grain filling period of wheat development and having an increased level of wheat heat stress peptide when exposed to elevated temperatures during the grain filling period, said wheat heat stress peptide further characterized as binding to monoclonal antibody MA3-006;
   (b) extracting said wheat heat stress peptide from said sample;
   (c) measuring the level of said extracted wheat heat stress peptide; and
   (d) comparing said measured level with said constitutive level and determining that said wheat grain has been exposed to elevated temperatures during the grain filling period if said measured level is two or more times greater than said constitutive level.

2. The method of claim 1 wherein said endosperm-containing sample is mature grain or flour.

3. The method of claim 1 wherein said sample comprises a mixture of varieties of wheat grain.

4. The method of claim 1 wherein said measuring comprises an immunoassay or an isotopic labelling assay.

5. The method of claim 4, wherein said immunoassay comprises contacting said sample extract with an antibody which binds said wheat heat stress peptide to obtain bound antibody and measuring said bound antibody as a measure of the level of said wheat heat stress peptide in said sample.

6. The method of claim 5 wherein said antibody is monoclonal antibody MA3-006.

7. An immunoassay for detecting wheat grain that has been exposed to elevated temperatures during the grain filling period, which comprises:
   (a) obtaining an endosperm-containing sample of mature wheat grain, said wheat endosperm having a constitutive level of wheat heat stress peptide when not exposed to elevated temperatures during the grain filling period of wheat development and having an increased level of wheat heat stress peptide when exposed to elevated temperatures during the grain fling period, said wheat heat stress peptide further characterized as binding to monoclonal antibody MA3-006;
   (b) extracting said wheat heat stress peptide from said sample;
   (c) reacting said extract with a reagent which selectively binds said wheat heat stress peptide;
   (d) reacting said bound wheat heat stress peptide with an immunologic binding partner which specifically binds said bound wheat heat stress peptide;
   (e) detecting said bound immunologic binding partner as a measure of the level of said wheat heat stress peptide in said sample; and
   (f) comparing said measured level with said constitutive level and determining that said wheat grain has been exposed to elevated temperatures during the grain filling period if said measured level is two or more times greater than said constitutive level.

8. A method for assessing an end-use property of wheat grain, which comprises:
   (a) measuring exposure of wheat grain to elevated temperatures during a grain filling period by the steps of: (i) obtaining an endosperm-containing sample of mature wheat grain, said wheat endosperm having a constitutive level of wheat heat stress peptide when not exposed to elevated temperatures during the grain filling period of wheat development and having an increased level of wheat heat stress peptide when exposed to elevated temperatures during the grain filling period, said wheat heat stress peptide further characterized as binding to monoclonal antibody MA3-006; (ii) extracting said wheat heat stress peptide from said sample; and (iii) measuring the level of said extracted wheat heat stress peptide;
   (b) comparing the measured level to a calibration curve that correlates the level of wheat heat stress peptide and an end-use property; and
   (c) based on the comparison of step (b), assessing whether said wheat grain is suitable for said end-use property.

* * * * *